United States Patent [19]
Cathignol et al.

[11] Patent Number: 5,479,928
[45] Date of Patent: Jan. 2, 1996

[54] ULTRASONIC METHOD AND APPARATUS FOR FLOW MEASUREMENT

[75] Inventors: Dominique Cathignol, Genas; Bernard Lavandier, Ambierle; Raoul Muchada, Lyons, all of France

[73] Assignee: Institut National de la Sante et de la Recherche Medicale, Paris, France

[21] Appl. No.: 387,385

[22] Filed: Feb. 13, 1995

Related U.S. Application Data

[63] Continuation of Ser. No. 64,900, May 24, 1993, abandoned.

[30] Foreign Application Priority Data

Sep. 21, 1992 [FR] France ..................... 92 11425

[51] Int. Cl.⁶ .................. A61B 8/12; A61B 8/06
[52] U.S. Cl. .................. 128/662.06; 128/662.04
[58] Field of Search ............ 73/660.04–660.05, 73/661.07–661.1, 662.04, 662.06, 713, 861.25

[56] References Cited

U.S. PATENT DOCUMENTS

| | | | |
|---|---|---|---|
| 3,977,247 | 8/1976 | Hassler | 128/661.09 |
| 4,095,597 | 6/1978 | Hassler | 128/661.09 |
| 4,391,148 | 7/1983 | Sainz et al. | 128/661.08 |
| 4,671,295 | 6/1987 | Abrams et al. | 128/662.06 |
| 4,757,822 | 7/1988 | Di Giuliomaria et al. | 128/661.07 |
| 5,085,220 | 2/1992 | Nudell et al. | 128/661.09 |
| 5,243,987 | 9/1993 | Shiba | 128/660.06 |

FOREIGN PATENT DOCUMENTS

| | | |
|---|---|---|
| 0363156 | 4/1990 | European Pat. Off. . |
| 2296165 | 7/1976 | France . |
| 2424733 | 11/1979 | France . |

OTHER PUBLICATIONS

Medical and Biological Engineering, MBE Letter, Vessel area detection with c.w. ultrasound, Mar. 1976, vol. 14.

Wildi, Eric, Knutti, James W., Allen, Henry V. and Meindl, James D.; "Dynamics and Limitations of Blood/Muscle Interface Detection Using Doppler Power Returns", vol. BME–27 (1980) Oct., No. 10, New York, USA.

Robert M. Olson and Julian P. Cooke, "A Nondestructive Ultrasonic Technique to Measure Diameter and Blood Flow in Arteries," *IEEE Transactions on Biomedical Engineering*, Mar. 1974.

Michael K. Wells et al., "Ultrasonic Transesophageal Measurement of Hemodynamic Parameters in Humans," *ISA Transactions*, vol. 18, No. 1, Sep. 1979.

M. B. Histand et al., "Ultrasonic Pulsed Doppler Transoesophageal Measurement of Aortic Haemodynamics in Humans," *Ultrasonics*, Sep. 1979.

*Primary Examiner*—Francis Jaworski
*Attorney, Agent, or Firm*—Popham, Haik, Schnobrich & Kaufman, Ltd.

[57] ABSTRACT

An ultrasonic probe for flow rate measurement by the Doppler effect includes at least one wide-beam ultrasound transducer fixed on a support block and at least one narrow-beam ultrasound transducer fixed on a support block and whose beam position is known in relation to the wide beam, and a control and processing unit which processes and measures the characteristics of the signal from the narrow-beam transducer in order to determine the only appropriate direction for pointing the wide-beam transducer to enable an accurate measurement of flow rate to be performed.

33 Claims, 2 Drawing Sheets

FIG_1

FIG_2

FIG_3

FIG_4

ULTRASONIC METHOD AND APPARATUS FOR FLOW MEASUREMENT

This application is a file wrapper continuation of U.S. patent application Ser. No. 08/064,900, filed May 24, 1993, and now abandoned.

FIELD OF THE INVENTION

The present invention relates to the technical field of ultrasound probes, in the wide meaning of the term, as used for measuring speed and/or flow rate, and it relates in particular to ultrasound probes suitable for in-body measurements, the probes being inserted into the human body via a natural orifice.

A particularly advantageous application of the invention lies in measuring aorta flow rate by means of a probe inserted in the esophagus.

BACKGROUND OF THE INVENTION

French patent No.2,424,733 describes an in-body probe constituted by a catheter forming a flexible sheath containing a flexible coupling cable connected at one of its ends to a support block on which at least one ultrasound transducer is mounted, which transducer is connected outside the catheter to a processing and control unit. The other end of the cable is secured to a rotary drive member for rotating the support block.

Such a probe can be used to determine speed by means of the Doppler effect, and if the diameter of a blood vessel is known by other means, it is thus possible to determine the flow rate of blood flowing within the vessel. It is recalled that flow rate is equal to the cross-section of the vessel multiplied by the mean speed of the velocity distribution inside the vessel.

Although the above-described probe has made considerable progress possible in the measurement of aorta flow rates, it nevertheless turns out that the flow rate measurements performed using such a probe are lacking in accuracy.

Such a probe measures the mean speed by use of an ultrasound transducer whose beam does not cover the entire area of the right cross-section of the vessel. In addition, in practice, it is difficult or even impossible to ensure that the probe is pointing in the right direction for the purpose of measuring flow rates. Wrong positioning of the probe can give rise to Doppler signals that have all of the appearances of the looked-for signals, but that give rise to inexact flow rate values. Because of wrong positioning, the ultrasound beam may also cover, in part, a zone lying outside the vessel, such that the measurement device takes moving elements into account that lie outside the vessel, and this constitutes a source of error.

It should also be observed that in the prior art device, the treatment performed on the Doppler signal is incapable of excluding movement of the walls of the vessel since all signals coming from moving targets situated anywhere along the ultrasound beam are taken into account.

Furthermore, during the heart beat cycle, and in particular during diastole, the velocity distribution profile includes zones of zero speed or of speeds that are so low as to be incapable of being measured by means of the probe and the processing device in combination. The mean velocity distribution measured in this way is therefore erroneous, since account is taken only of targets that are moving fast enough. Under such conditions, flow rate measurement can give rise to an error that is extremely large given that the measured mean speed is multiplied over the entire cross-section of the vessel. The greater the relative fraction of the total cross-section of the vessel that is occupied by liquid streams that are stationary or too slow to be detected by the probe, the greater the error.

OBJECTS AND SUMMARY OF THE INVENTION

The present invention therefore seeks to remedy the above drawbacks by proposing a method and a probe capable of considerably increasing the accuracy with which the velocity distribution of a moving target is measured in order to measure the flow rate of the target accurately, and in particular in order to measure aorta flow rate accurately.

Another object of the invention is to provide a method and a probe suitable for providing accurate speed measurement exclusively over the entire cross-section of the moving target.

Another object of the invention is to provide a method and a probe capable of performing accurate speed measurements, and consequently accurate flow rate measurements, in a fluid, comprising particles in suspension, flowing-within a duct, notably aorta, this flow being optionally in particular of the pulsed type and therefore having at some instants a substantially zero speed or even a retrograde flow.

Another object of the invention is to provide a method and a probe capable of performing accurate speed measurements, and consequently accurate flow rate measurements, of blood in aorta. Advantageously, the solution has to enable to measure the speed and therefore the flow rate in the aorta by the use of the endocavitary type, inserted in the esophagus up to be positioned in front of the aorta, both during diastole and during systole, even when the flow rates are presenting liquid veins of variable flow rates, notably due to an irregular flow rate or a pulsed flow rate, which may include zero speed or retrograde flow(s).

To achieve the above objects, the probe includes at least one support block on which at least one ultrasound transducer is mounted, said transducer being connected to a processing and control unit.

According to the invention, it is provided a probe for accurately measuring the speed or the flow rate of a fluid containing particles in suspension flown with said fluid flowing in a given duct, comprising at least a support block on which at least one ultrasound transducer is mounted, said transducer being connected to a processing and control unit, characterized in that it comprises:

- at least one wide-beam ultrasound transducer, fixed on said support block to be orientable in rotation in direction of said duct to measure, by the Doppler effect, the speed of said fluid flowing in said duct;
- at least one narrow-beam ultrasound transducer, mounted in said probe to have its beam in a known relative position with respect to that of said wide-beam ultrasound transducer while being also orientable in rotation in direction of said duct; and
- a control and processing unit comprising measuring means for measuring and processing the characteristics of the signal from the narrow-beam transducer to determine a substantially accurate measure of the speed of substantially all of the fluid zones flowing in said duct, or in an angular field of low amplitude within which the measured speed on the cross-section of said duct is not influenced by a low angular position difference of said probe within said field.

According to a particular embodiment, the narrow-beam ultrasound transducer is mounted in said probe to have its beam orientable within a plane which is substantially perpendicular to the longitudinal axis of said duct and cutting said duct.

According to another particular embodiment, the narrow-beam ultrasound transducer and the wide-beam ultrasound transducer have a common symmetry plane.

According to another particular embodiment, the wide-beam ultrasound transducer and the narrow-beam ultrasound transducer are mounted on a single support block, and oriented one relative to the other, to have their beam or the average axis of said beam offset by a divergent angle, the wide-beam transducer being orientable with respect to said duct to present an inclination angle θ with respect to said longitudinal axis of said duct, to provide said Doppler effect, whereas the narrow-beam transducer is in an orientable position, according to a direction substantially perpendicular to the longitudinal axis of said duct and cutting said duct, to determine the relative precise position of said transducers or said support block in relation to said duct.

According to another particular embodiment, the means for measuring and processing the signal from the narrow-beam transducer comprises means for determining the proximal position or the distal position or both the distal and proximal position of the walls of said duct in the cutting plane performed by said narrow-beam transducer.

According to another particular embodiment, the means for measuring and processing the signal from the narrow-beam transducer comprise means for determining the amplitude of the signals received by the narrow-beam transducer and means for detecting the amplitude maxima of such signals which correspond respectively to the proximal wall or to the distal wall or both to the proximal and distal walls of said duct within said cutting plane.

According to another particular embodiment, the control and processing unit comprises calculating means for determining the distance range ($P_2$–$P_1$) corresponding to the proximal wall and the distal wall of said duct cutting plane performed by the wide-beam transducer, from the knowledge of the divergent angle (θ) as well as the distance between the proximal wall and the distal wall of said conduit within the cutting plane of the narrow-beam transducer, and selecting means for selecting the signals received by the wide-beam transducer, in the distance range ($P_2$–$P_1$) determined by said calculating means.

According to another particular embodiment, the probe is characterized in that it comprises rotating means for rotating said transducer(s) in relation to said duct, to determine the wished orientation for which the narrow-beam transducer is oriented substantially perpendicularly to the longitudinal axis of said duct and cutting said duct.

According to another particular feature of said probe, said probe is characterized in that the control and processing unit comprises signal processing means for processing signals received from the narrow-beam transducer to determine the orientation of said wide-beam transducer for which the number of particles in suspension in the volume defined by the intersecting of said wide-beam and said duct is maximized.

According to another particular embodiment, the control and processing unit also comprises speed or energy measuring means for measuring the speed and/or the backscattered energy by the particles in suspension in the fluid flowing within said duct, controlled by:

means for determining given instants where the speed and/or the backscattered energy are measured, one of said instants corresponding to a maximum backscattered energy resulting from a maximum of particles detected in movement within the measuring volume of said wide-beam transducer at that instant and other instants corresponding to instantaneous backscattered energy measures; and correcting means for correcting the speed or the flow rate by a factor that depends on the instantaneous backscattered energy at each instant and on the maximum backscattered energy during the instant where all the particles in suspension contained in a transverse cross-section are in movement.

According to another particular embodiment, the control and processing unit comprises means for comparing the respectively maximal and instantaneous backscattered energies with a given threshold (N) from the speed correction or flow rate correction is performed.

In particular, the given threshold lies in the range of 10% to 50% of the maximum backscattered energy ($E_S$), and preferably is about 25%.

According to another advantageous invention embodiment, said probe is characterized in that it comprises a catheter forming a flexible sheath containing a flexible coupling cable connecting at one of its end to the support block for the transducers, which are connected outside the catheter to the control and processing unit, the other end of the cable being connected to a rotating member for rotating individually said transducers relatively to the longitudinal axis of said probe.

According to a second aspect, the present invention also provides a method of measuring the speed or the flow rate of a fluid comprising particles in suspension, flowing within a duct having at least one cross-section (S) close to the full cross-section of said duct that is scanned by at least one ultrasound sensor, wherein said method comprises:

measuring the total backscattered energy ($E_S$) of all of the particles in suspension in said fluid, when all or substantially all of said particles are considered to be in movement, the cross-section ($S_S$) being the cross-section occupied by said particles in movement inside (S);

measuring the partial backscattered energy ($E_D$) at any instant of the particles in movement when only a part of said particles is considered to be in movement, the cross-section occupied by said particles in movement being equal to ($S_D$) lower to ($S_S$);

measuring the apparent average speed of all of said particles in movement occupying the full cross-section or the partial cross-section of said duct and optionally measuring the apparent average flow rate by multiplying the apparent speed by the total cross-section of said duct; and correcting the speed or flow rate measurement by a factor that depends on the partial energy ($E_D$) and the total energy ($E_S$).

According to a particular feature of the method, said method is characterized in that it comprises correcting the speed or the flow rate only when the measured energy is lower than a given threshold (N) lying between 10% and 50% and, preferable to about 25%, of the maximum backscattered energy.

According to another particular feature, said process is characterized in that it comprises measuring and averaging the total backscattered energy ($E_S$) over a plurality of cycles during which all of the particles in movement occupy all or substantially all the total cross-section of said duct.

According to another particular feature, said method is characterized in that it comprises correcting the measure of speed or of flow rate by a correction factor depending from the ratio of the partial energy ($E_D$) divided by the total energy ($E_S$), the correction factor (K) being weighted by a correction coefficient dependent from the characteristics of the wide-beam transducer and from the measuring means for measuring the speed and/or the energy.

According to another advantageous feature, said method may further be characterized in that said fluid is flowing in said duct in a pulsed manner, and in particular presents instants where the speed reaches substantially zero and even a retrograde flow.

According to a third aspect, the present invention also provides a method for measuring the speed or the flow rate of blood in aorta with at least one ultrasound transducer, characterized in that it comprises the steps of:

measuring the total backscattered energy ($E_S$) of hematies in movement in said blood, when all or substantially all the hematies are considered to be in movement, at orthogonal total cross-section of said aorta;

measuring the partial backscattered energy ($E_D$) at every instant by the hematies of the blood flowing in said aorta, when only a part of said hematies is considered to be in movement, the cross-section occupied by said hematies in movement being equal ($S_D$) lower to (S);

measuring the apparent average speed at any instant of flow of hematies in aorta, optionally calculating the apparent average flow rate by multiplying said average speed by the full cross-section of said aorta; and correcting the measurement of the speed and/or the flow rate by a factor dependent from the partial energy ($E_D$) and the total energy ($E_S$).

According to a particular feature, said method is characterized in that the total backscattered energy ($E_S$) is substantially synchronized to systole.

According to another particular feature, said method comprises measuring the total cross-section of said aorta with a narrow-beam ultrasound transducer located substantially perpendicularly to the longitudinal axis of said aorta and intersecting said axis; measuring the instantaneous speed at a given instant with a wide-beam ultrasound transducer located at an angle (θ) relatively to said narrow-beam ultrasound transducer, by Doppler effect, and only selecting the speed of hematies in movement located inside the aorta, excluding the aorta walls.

According to another particular feature, said method comprises correcting the speed or the flow rate only when the measured energy is lower than a given threshold (N) ranging between 10 and 50% and, preferably, of the order of 25%, of the maximal backscattered energy.

According to another particular feature of said method, said method comprises measuring and averaging the total backscattered energy ($E_S$) over several cycles during which the hematies in movement occupy substantially the total cross-section of the aorta.

According to another particular feature of said method, said method comprises correcting the measurement of the speed or of the flow rate by a correction factor (K) depending from the ratio between the partial energy ($E_D$) divided by the total energy ($E_S$), the correction factor (K) being weighted by a correction coefficient dependent from the features of the wide-beam transducer and measuring means for measuring speed and/or energy.

According to another particular advantageous feature of said method, said probe is an endocavitary probe and is introduced in esophagus to be positioned in front to aorta.

According to the invention, the probe makes it possible to perform measurements exclusively on the full cross-section of a given medium or duct, such as the aorta.

BRIEF DESCRIPTION OF THE DRAWINGS

Various other characteristics appear from the following description given with reference to the accompanying drawings that show embodiments and implementations of the invention by way of non-limiting example.

MORE DETAILED DESCRIPTION

Figure 1:
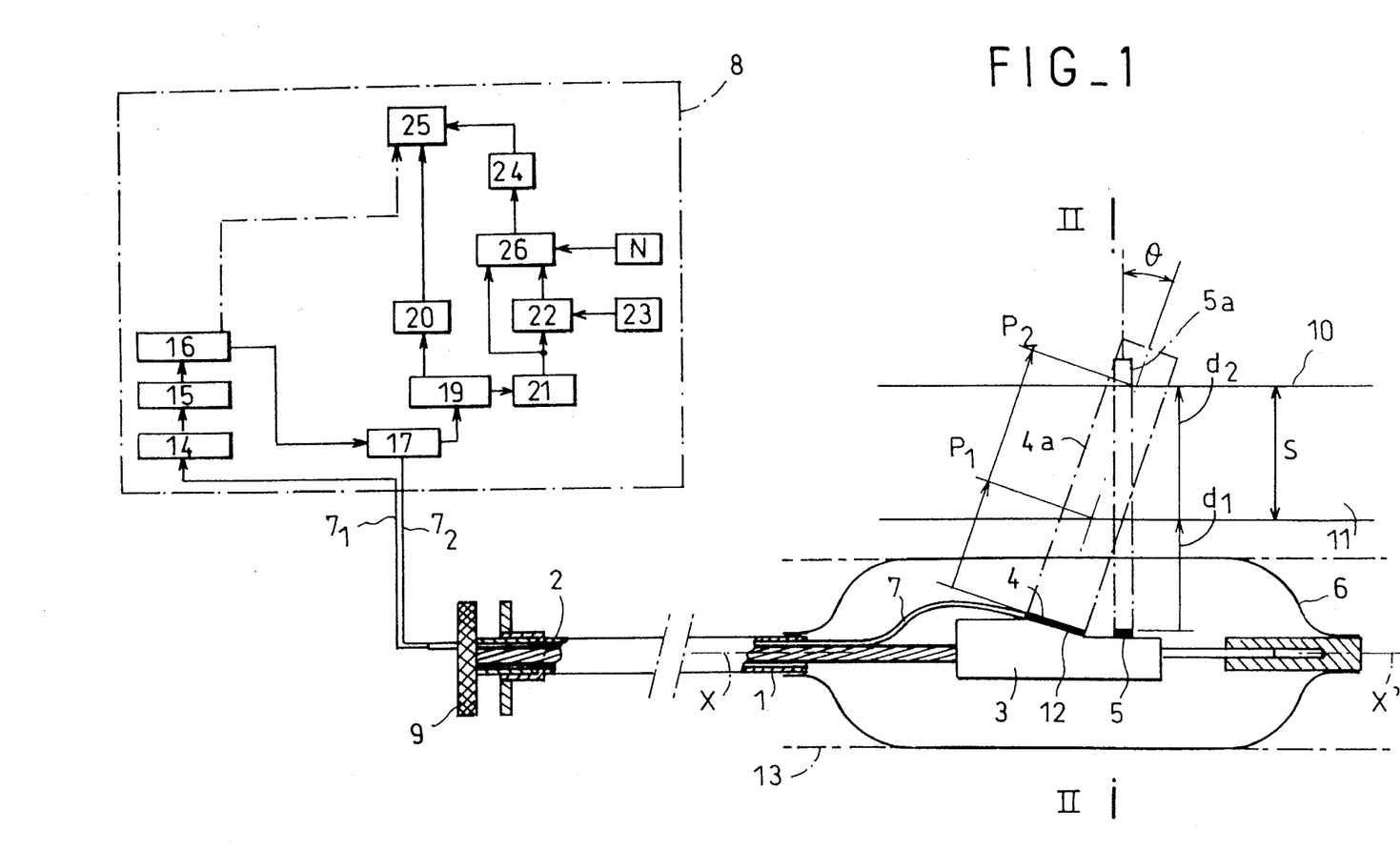
FIG. 1 is an elevation view in section through an embodiment of the invention.

FIG. 1 shows an embodiment of a probe in accordance with the invention for the purpose of performing in-body measurements of speed and/or flow rate. To this end, the in-body probe comprises a catheter 1 forming a sheath or flexible tube which is made in conventional manner from materials that are selected for their characteristics of non-toxicity and of being well tolerated by mucous membranes. The sheath 1 contains a flexible coupling cable 2 which is connected at one of its ends to at least one support block 3 on which ultrasound transducers 4 and 5 are mounted. In conventional manner, this end of the probe 1 which is designed to be inserted in the body is provided with a balloon 6 surrounding the support block 3. The transducers 4 and 5 axe connected to an electric cable 7 placed inside the sheath 1 and extending outside the catheter for connection to a unit 8 for controlling the transducers and for processing the signals delivered thereby. The end of the cable 2 opposite to its end provided with the support block 3 is connected to a drive member 9 such as a knurled knob for rotating the flexible cable 2 about its own axis.

According to a characteristic of the invention, the support block 3 is designed to receive at least one ultrasound transducer 4 that presents a "wide" beam 4a, i.e. a beam adapted to cover at least the entire cross-section S of a medium 10 such as a vessel that preferably constitutes the aorta and that is occupied by a moving target 11 which is formed by a flow of blood (FIG. 2), for example. The transducer 4 is placed on a support plane 12 formed on the support block 3. When the probe is designed to be inserted into the esophagus to enable aorta flow rate to be measured, the transducer 4 is inclined relative to the common longitudinal axis x-x' of the cable 2 and of the support block 3 in such a manner as to enable blood speed to be detected by the Doppler effect. For example, the transducer 4 used may be a P1 60 type transducer in the form of a 4 mm by 4 mm cylindrical sector having a radius of curvature of 6 mm and sold by the firm "Quartz et Silice".

According to the invention, the support block 3 is also fitted with an ultrasound transducer 5 that presents a beam 5a which can be considered as being narrow relative to the cross-section S of the aorta 10 and relative to the beam 4a. The transducer 5 is of the type that produces a localized or plane beam and it is mounted on the support block 3 in such a manner that its beam 5a is preferably centered on the plane of symmetry P of the wide beam, i.e. passing through the axis x-x'. The narrow beam 5a is offset by a divergent angle θ relative to the wide beam 4a and it preferably points along a direction that is substantially perpendicular to the axis x-x'.

Naturally, it must be considered that the transducer 5 can be fixed to the support block 3 in such a manner that its beam 5a is in some other known position relative to the wide beam 4a. Furthermore, the transducers 4 and 5 could be mounted on distinct support blocks providing their relative positions are known, in particular by construction.

The probe described in the example shown is designed to be inserted via a natural orifice into a natural duct, e.g. the esophagus 13 which is represented by chain-dotted lines, and then to be displaced axially along the duct so that the transducers 4 and 5 are moved to face a cross-section S of the aorta 10. The support block 3 is then itself displaced by means of the drive knob 9 which transmits its force via the cable 2, thereby enabling the transducers 4 and 5 to be appropriately pointed in azimuth.

In order to place the wide beam 4a in a position where it covers the entire cross-section of the vessel 10 to be scanned, the narrow-beam transducer 5 is connected to the unit 8 which includes means for measuring and processing the characteristics of the signal produced by the narrow-beam transducer 5.

To this end, the control and processing unit 8 includes determining means 14 connected to the transducer 5 by a link $7_1$, and designed to determine the amplitude of the signals received as echoes by the narrow-beam transducer 5. The determining means 14 are connected to means 15 designed for detecting amplitude maxima in the reflected signals. In conventional manner, it should be considered that the echoes from the transducer 5 are of maximum amplitude when the beam 5a is perpendicular to the walls of the vessel 10. The support block 3 is displaced in azimuth by means of the knob 9 until it occupies a position in which the echoes of the signal from the transducer 5 appear to go through a maximum amplitude. The transducer 4 then points in the appropriate direction by construction, such that its wide beam 4a applies sound to the entire cross-section S of the aorta 10. It is thus possible to ensure that the probe points in a single and correct direction insofar as the amplitude of echoes from the walls decreases considerably for a small amount of angular deflection. It should also be observed that the ultrasound transducer 4 makes it possible to measure speed over the entire cross-section of the vessel 9 insofar as all of said cross-section receives sound from the wide beam 4a.

When two narrow-beam transducers 5 are used, it is alternatively possible to determine that the wide-beam transducer 4 is pointing in an appropriate direction by seeking a position in which the signals from the two transducers 5 are of equal amplitude, for example.

In order to further increase the accuracy of speed measurements performed by the transducer 4, provision is made to take account solely of echoes from the transducer 5 that come from a range $P_2-P_1$ defining two opposite end points of the cross-section of the aorta 10. To this end, the control and processing unit 8 includes means 16 designed to determine said range $P_2-P_1$. The means 16 are connected to the means 15 in order to determine a range $d_2-d_1$ corresponding to the two end points of the aorta as detected from the amplitude maxima of echoes relating to signals from the transducer 5. Given the range $d_2-d_1$, it is possible to calculate the cross-section of the vessel which is known or assumed to be circular in section.

Thereafter, the determination means 16 determine the range $P_2-P_1$ from the range $d_2-d_1$ and the angle of divergence θ between the two beams which is known, in particular by construction. These determination means 16 control selection means 17 connected to the transducer 4 by a link $7_2$. The selection means 17 serve to select only those echoes of the signals from the transducer 4 that lie within a range of response times that correspond to the range $P_2-P$. The selection means 17 are connected to conventional processing means 19 that serve to obtain a Doppler signal. The processing means 19 are connected to conventional means 20 for determining the mean velocity distribution $V_m$ of blood flowing through the cross-section of the aorta 10.

The combined use of at least one wide-beam transducer 4 and at least one narrow-beam transducer 5 makes it possible to measure speeds over the entire cross-section of the aorta 10 without taking account of elements located outside such a vessel. The speed measurement field thus coincides as closely as possible with the cross-section S of the aorta.

According to an advantageous characteristic of the invention, the probe is suitable for performing accurate measurements of mean velocity distribution that take account of the cross-sectional area of liquid streams that are travelling at a speed that is zero or so small as to be considered as being zero by the means 19 and 20 operating in conventional manner. The probe of the invention is thus suitable for performing speed measurements that take account of the effective or real cross-section occupied by the red corpuscles under consideration that are moving within the aorta.

Figure 3:
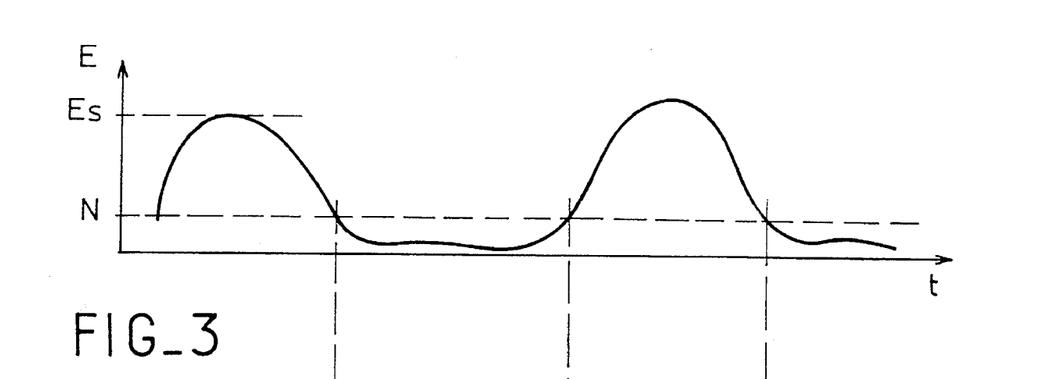
FIG. 3 is a waveform diagram showing the energy backscattered by the moving target as a function of time.

To this end, the unit 8 includes energy calculation means 21 suitable for measuring the energy backscattered by moving particles, in particular red corpuscles in blood. The backscattered energy E is proportional to the number of moving corpuscles and is measured continuously so as to discover the mass of liquid that is in motion (FIG. 3). Thus, the energy E of the received signal is given by the following equation:

$$E=e.c.l.S.$$

where c is particle concentration, i.e. red corpuscle concentration, e is the energy backscattered by a single particle, and the product I.S. is the measurement volume containing the particles in motion.

The energy calculation means 21 which receive the Doppler signal from the processing means 19 determine at each instant the amplitude or energy E that is backscattered from the moving targets. The amplitude of the Doppler signal is proportional to the square root of the backscattered energy. The output from the calculation means 21 is connected to means 22 designed to determine the value of the energy appearing at one or more defined instants, in particular during systole. The means 22 are thus connected to means 23 suitable for determining the instants at which systole takes place. In conventional manner, systole can be detected on the basis of maximum blood speed, on the basis of the backscattered energy, or on the basis of an electrocardiogram.

The means 22 therefore deliver the value of the energy $E_S$ backscattered during systole. The energy $E_S$ backscattered during systole is preferably measured over a plurality of heart cycles, e.g. about ten cycles, and is then averaged, in order to take account of normal physiological variations.

It should be considered that during systole all of the red corpuscles (hematies) are in motion, such that the total energy $E_S$ backscattered at said instant corresponds to the motion of the targets occupying the total cross-section S of the vessel. At times other than systole, and in particular during diastole, the cross-sectional areas $S_D$ covered by the particles that are indeed in motion may be less than the total cross-section S.

By taking account of the energy backscattered both during systole $E_S$ and during diastole $S_D$, it is possible to determine the real or theoretical cross-sectional area $S_D$ that contributes to the flow. This area is such that:

$$S_D = S \cdot (E_D E_S) = S \cdot K.$$

The correction factor K is determined by correction means 24 connected to the means 21 and 22. Advantageously, the correction means 24 weight the factor K by a practical correction coefficient which takes account of the technical characteristics of the transducer 4 that is in use and of the means emitting, receiving, measuring and processing the signals related to the Doppler tranducer 4, including means 19, in particular the minimum value of the speeds detected and the passband of the Doppler signal. These correction means 24 are connected to means 25 which are in turn connected to the means 20 for determining the mean velocity distribution. These means 25 respond to the values of the mean velocity distribution and of the correction factor K to calculate the corrected mean speed $V_c$, and consequently the flow rate of the blood moving through the localized cross-sectional area $S_D$ on the basis of knowledge of the cross-section of the vessel.

Figure 4:
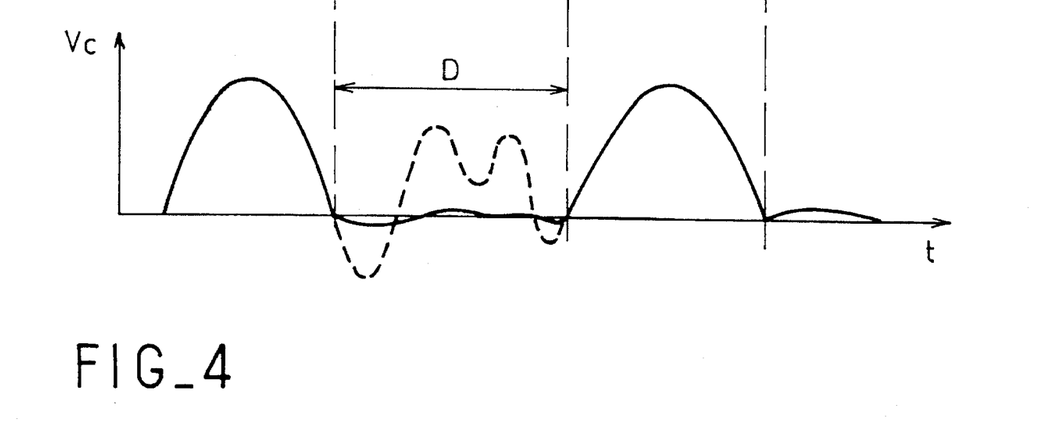
FIG. 4 shows one example of a speed curve as a function of time, and as obtained by the probe of the invention, both before and after correction.

FIG. 4 shows an example of a curve giving the corrected speed $V_c$ as a function of time. This curve makes it possible to understand the correction performed on the basis of the raw measured speeds which are represented by dashed lines during diastole D. The method of the invention makes it possible to obtain high accuracy on speed measurements, and consequently on blood flow rate measurements, since the measured values take account of the cross-section that actually contributes to blood flow.

As can be seen more particularly in FIG. 3, the correction factor determined by the means 24 is applied only when the backscattered energy is below a given threshold N, which threshold may be fixed or adjustable, thereby taking account simultaneously of physiological variations and of statistical variations that are normal in the Doppler signal and that are known from elsewhere. Advantageously, the threshold N lies in the range 10% to 50% of the maximum energy $E_S$ backscattered during systole, and is preferably about 25%. Such a comparison performed by means 26 interposed between the means 21–22 and 24 makes it possible at each instant during the heart cycle to correct the speed and flow rate values, particularly during diasrole d, as can be seen more clearly in FIG. 4.

Naturally, the various component means of the unit 8 may be implemented in programmed or in hard-wired form. In addition, it should be observed that the various circuits required for the operation of the transducers 4 and 5 are not described in greater detail since they not form part of the invention and they are known per se. Furthermore, it should be considered that the above description relates to an in-body probe. Naturally, it is clear that the invention is applicable to an out-of-body probe. Under such circumstances, the probe no longer includes a catheter 1 and a flexible coupling cable 2. For example, such a probe may be designed for measuring the flow rate of the ascending aorta by the sustemal path.

Figure 2:
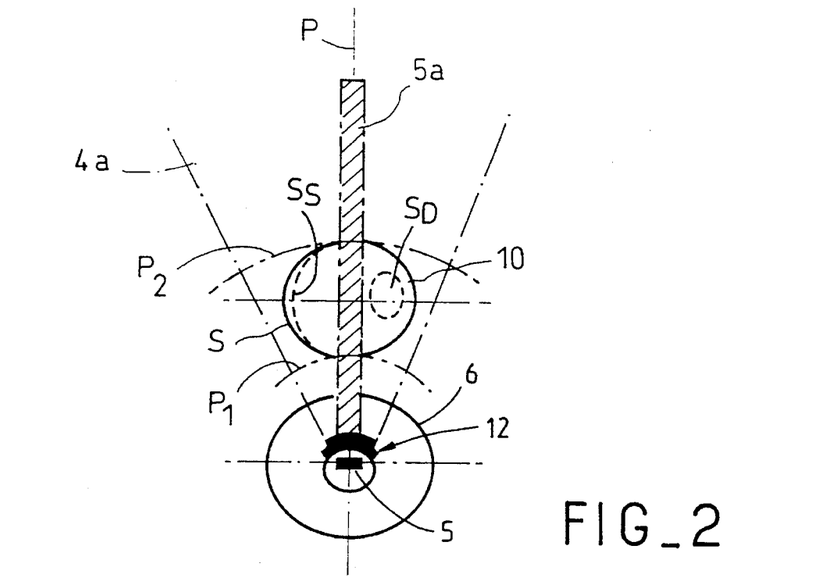
FIG. 2 is a projection view of the cross-section taken substantially on line II—II of FIG. 1, showing a characteristic detail of the invention.

In the drawings, the cross-section $S_S$ is defined by the cross-section occupied by the particles in suspension in the duct, for instance the hematies in aorta, when all or substantially all am considered in movement, within the cross-section scanning plane of the wide-beam transducer 4, said cross-section $S_S$ being substantially equal to the cross-section S of the scanned duct, hem aorta, as shown in FIG. 2. Partial cross-section $S_D$ is the cross-section occupied at every instant by the particles in suspension in the duct, for instance the hemaries, detected as being in movement and which can represent a very localized zone as shown in FIG. 2.

With regard to the correction factor K, said correction factor K may in one examplary embodiment be represented by the following formula:

$$K = \left( \frac{E_D}{E_S} \right)^n \times k$$

wherein:
K=correction factor
$E_D$=backscattered partial energy as previously defined
$E_S$=total backscattered energy as previously defined
n is a number constituting another correcting coefficient
k is a correction coefficient as previously defined dependent from the technical characteristics of the transducer 4 and of the means emitting, receiving, measuring and processing the signals related to the Doppler transducer 4, including the measuring means 19.

When measuring the speed flow of blood in aorta, the following values were obtained on two patients:

with the probe according to the invention, the correction coefficient k is equal to 1, n is ½ and the threshold N was fixed at 25% of the maximum backscattered energy ($E_S$).

On these two patients, the signals received by the transducers of the invention probe were registered and subject to computer calculations and gave the following values of speed measures:

A—for patient A, having a diameter of aorta of 3 cm:
.average speed on 500 measures of instantaneous speed, non corrected: 8.64 cm/second.

On the registered curve, which was performed during 10 seconds, it was observed that the measures concerning the partial cross-section $S_D$ were in majority negative.

Since this threshold was applicable, a correction of the average speed was performed providing a corrected speed average value of 9.3 cm/second.

A second testing was later performed on the same patient A and the values were as follows:

average speed on 500 measures of instantaneous speed during 10 seconds, non corrected: 9.66 cm/second.

It was observed that in majority, the localized flows $S_D$ were positive and further that the threshold was applicable.

The corrected average speed was therefore of 9.03 cm/second.

B—For a second patient B, having a diameter of aorta of 2.4 cm, in the same conditions, the speed values were as follows:

non corrected average speed: 18.6 cm/second.

With said patient B, the localized flows $S_D$ were in majority positive and the threshold was also applicable.

The corrected speed value was of 15.36 cm/second.

The invention is not limited to the examples described and shown since numerous modifications can be made thereto without going beyond the scope of the invention.

The invention covers any technical feature, which appears to be novel from the whole description and claims, including the drawings. The drawings axe an integral part of the invention, and therefore of the present specification.

We claim:

1. A probe for accurately measuring the speed or the flow rate of a fluid containing particles suspended in said fluid flowing in a given duct having a longitudinal axis, said probe having a longitudinal axis, and comprising:

(a) at least one narrow-beam ultrasound transducer fixed on a support block provided with rotation means to rotate said at least one narrow-beam transducer in a direction of said duct and to position said at least one narrow-beam transducer with its narrow-beam cutting said duct according to a cutting plane substantially perpendicular to the longitudinal axis of said duct:

(b) at least one wide-beam ultrasound transducer mounted in said probe to have its wide beam in a known relative position with respect to that of said at least one narrow-beam ultrasound transducer, rotation means being also provided to rotate said at least one wide-beam ultrasound transducer in the direction of said duct to measure, by the Doppler effect, the speed of said fluid flowing in said duct;

(c) a control and processing unit comprising processing means for processing the characteristics of the signal(s) from said at least one narrow-beam transducer, the control and processing unit also comprising speed and/or energy measuring means for measuring the speed and/or the backscattered energy ($E_s$) by the particles in suspension in the fluid flowing within said duct, controlled by:

means for determining given instants where the speed and/or the backscattered energy are measured, one of said instants corresponding to a maximum backscattered energy resulting from a maximum of particles detected in movement within the measuring volume of said at least one wide-beam transducer at that instant and other instants corresponding to instantaneous backscattered energy measures; and correcting means for correcting the speed or the flow rate by a factor that depends on the instantaneous backscattered energy at each instant and on the maximum backscattered energy during the instant where all the particles in suspension contained in a transverse cross-section are in movement.

2. A probe according to claim 1, wherein the control and processing unit comprises means for comparing the respectively maximal and instantaneous backscattered energies with a given threshold (N) from which the speed correction or flow rate correction is performed.

3. A probe according to claim 2, wherein the given threshold lies in the range of 10% to 50% of the maximum backscattered energy ($E_s$), and preferably is about 25%.

4. A method of measuring the speed or the flow rate of a fluid comprising particles in suspension, flowing within a duct having a cross-section (S) close to the full cross-section of said duct that is scanned by at least one ultrasound sensor, wherein said method comprises:

measuring the total backscattered energy ($E_s$) of all of the particles in suspension in said fluid, when all or substantially all of said particles are considered to be in movement, the cross-section ($S_S$) being the cross-section occupied by said particles in movement inside (S);

measuring the partial backscattered energy ($E_D$) at any instant of the particles in movement when only a part of said particles is considered to be in movement, the cross-section occupied by said particles in movement being equal to ($S_D$) lower to ($S_S$);

measuring the apparent average speed of all of said particles in movement occupying the full cross-section or the partial cross-section of said duct; and correcting the speed measurement by a factor that depends on the partial energy ($E_D$) and the total energy ($E_S$).

5. A method according to claim 4, further comprising the step of correcting the speed only when the measured energy is lower than a given threshold (N) that is between 10% and 50% of the maximum backscattered energy.

6. A method according to claim 4, comprising measuring and averaging the total backscattered energy ($E_S$) over a plurality of cycles during which all-of the particles in movement occupy all or substantially all the total cross-section of said duct.

7. A method according to claim 4, further comprising the step of correcting the measurement of speed by a correction factor that varies according to a ratio of the partial energy ($E_D$) to the total energy ($E_S$), the correction factor (K) being weighted by a correction coefficient that varies according to characteristics of a wide ultrasound beam provided by said at least one ultrasound transducer and to the measuring means for measuring the speed and/or the energy.

8. The method of claim 4, which is a method of measuring the speed or the flow rate of a fluid which is flowing in said duct in a pulsed manner, and in particular presents instants where the speed reaches substantially zero and even a retrograde flow.

9. A method according to claim 4, for measuring the speed or the flow rate of blood in an aorta with at least one ultrasound transducer, further comprising the steps of:

measuring the total backscattered energy ($E_S$) of hemaries in movement in said blood, when all or substantially all the hemaries are considered to be in movement, at orthogonal total cross-section of said aorta;

measuring the partial backscattered energy ($E_D$) at every instant by the hemaries of the blood flowing in said aorta, when only a part of said hemaries is considered to be in movement, the cross-section occupied by said hemaries in movement being equal ($S_D$) lower to (S);

measuring the apparent average speed at any instant of flow of hemaries in said aorta; and correcting the measurement of the speed and/or the flow rate by a factor that varies according to the partial energy ($E_D$) and the total energy ($E_S$).

10. The method of claim 9, wherein the total backscattered energy ($E_S$) is substantially synchronized to systole.

11. The method of claim 9, comprising measuring the total cross-section of said aorta with a narrow-beam ultrasound transducer located substantially perpendicularly to the longitudinal axis of said aorta and intersecting said axis; measuring the instantaneous speed at a given instant with a wide-beam ultrasound transducer located at an angle (θ) relatively to said narrow-beam ultrasound transducer, by Doppler effect, and only selecting the speed of hemaries in movement located inside the aorta, excluding the aorta walls.

12. The method of claim 9, further comprising the step of correcting the speed only when the measured energy is lower than a given threshold (N) ranging between 10% and 50% of the maximal backscattered energy.

13. The method of claim 9, comprising measuring and averaging the total backscattered energy ($E_S$) over several cycles during which the hemaries in movement occupy substantially the total cross-section of the aorta.

14. The method of claim 9, further comprising the step of correcting the measurement of the speed by a correction factor (K) that varies according to the ratio between the partial energy ($E_D$) to the total energy ($E_S$), the correction factor (K) being weighted by a correction coefficient that varies according to the features of a wide-beam provided by said transducer and measuring means for measuring speed and/or energy.

15. The method of claim 9, wherein the probe is an endocavitary probe and is introduced in esophagus to be positioned in front to aorta.

16. A method according to claim 9, wherein said step of measuring the apparent average speed includes calculating the apparent average flow rate by multiplying said average speed by the full cross-section of said aorta.

17. A method according to claim 4, wherein said step of measuring the apparent average speed includes measuring the apparent average flow rate by multiplying the apparent speed by the total cross-section of said duct.

18. A probe for accurately measuring the speed or the flow rate of a fluid containing particles suspended in said fluid flowing in a given duct having a longitudinal axis and a wall, said probe having a longitudinal axis, and comprising:

(a) at least one narrow-beam ultrasound transducer fixed on a support block provided with rotation means to rotate said at least one narrow-beam transducer in a direction of said duct and to position said at least one narrow-beam transducer with its narrow beam cutting said duct according to a cutting plane substantially perpendicular to the longitudinal axis of said duct;

(b) at least one wide-beam ultrasound transducer mounted in said probe to have its wide beam in a known relative position with respect to that of said at least one narrow-beam ultrasound transducer, rotation means being also provided to rotate said at least one wide-beam ultrasound transducer in the direction of said duct to measure, by the Doppler effect, the speed of said fluid flowing in said duct;

(c) a control and processing unit comprising processing means for processing the characteristics of the signal(s) from said at least one narrow-beam transducer to determine the perpendicular position of said at least one narrow-beam transducer with respect to the wall of the duct, said control unit controlling the working of said at least one wide-beam transducer to measure the speed of said fluid flowing in said duct in that position of said at least one narrow-beam transducer, thereby determining a substantially accurate measure of the speed of substantially all the fluid flowing in said duct.

19. A probe according to claim 18, wherein said at least one narrow-beam transducer and said at least one wide-beam transducer have a common symmetry plane.

20. A probe according to claim 18, wherein said at least one wide-beam ultrasound transducer and said at least one narrow-beam ultrasound transducer are mounted on a single support block, and oriented one relative to the other, to have their beam or the average axis of said beam offset by a divergent angle, said rotation means being provided for simultaneous rotation of the transducers about the longitudinal axis of said probe.

21. A probe according to claim 18, wherein the means for processing the characteristics of the signal from said at least one narrow-beam transducer comprises means for determining the amplitude of the signals received by said at least one narrow-beam transducer and means for detecting the amplitude maxima of such signals which correspond to the wall of said duct.

22. A probe according to claim 18, further comprising a catheter forming a flexible sheath containing a flexible coupling cable connected at one of its ends to the support block for the transducers and adapted to connect at the other of its ends outside the catheter to the control and processing unit, the other end of the cable being connected to a rotating member for rotating said transducers relatively to the longitudinal axis of said probe.

23. A probe, according to claim 18, wherein said duct is a blood vessel and said probe is adapted to measure the flow of blood in said blood vessel.

24. A probe for accurately measuring the speed for the flow rate of a fluid containing particles suspended in said fluid flowing in a given duct having a longitudinal axis and a wall, said probe having a longitudinal axis, and comprising:

(a) at least one narrow-beam ultrasound transducer fixed on a support block provided with rotation means to rotate said at least one narrow-beam transducer in a direction of said duct and to position said at least one narrow-beam transducer with its narrow beam cutting said duct according to a cutting plane substantially perpendicular to the longitudinal axis of said duct;

(b) at least one wide-beam ultrasound transducer mounted in said probe to have its wide beam in a known relative position with respect to that of said at least one narrow-beam ultrasound transducer, rotation means being also provided to rotate said at least one wide-beam ultrasound transducer in the direction of said duct to measure, by the Doppler effect, the speed of said fluid flowing in said duct;

(c) a control and processing unit comprising processing means for processing the characteristics of the signal(s) from said at least one narrow-beam transducer, the means for processing the signals from said at least one narrow-beam transducer comprising means for determining at least the distal position of the wall of the duct in the cutting plane performed by said at least one narrow-beam transducer, said processing means determining the position of said at least one narrow-beam transducer for which echoes of at least the distal position of the wall are received at the amplitude maxima, said control unit controlling the working of said at least one wide-beam ultrasound transducer to measure the speed of said fluid flowing in said duct in that position of said at least one narrow-beam ultrasound transducer, thereby determining a substantially accurate measure of the speed of substantially all the fluid flowing in said duct.

25. A probe according to claim 24, wherein the control and processing unit comprises signal processing means for processing signals received from said at least one narrow-beam transducer to determine the orientation of said at least one wide-beam transducer for which the number of particles in suspension in the volume defined by the intersecting of said wide-beam and said duct is maximized.

26. A probe, according to claim 24, wherein said duct is a blood vessel and said probe is adapted to measure the flow of blood in said blood vessel.

27. A probe for accurately measuring the speed or the flow rate of a fluid containing particles suspended in said fluid flowing in a given duct having a longitudinal axis and a wall, said probe having a longitudinal axis, and comprising:

(a) at least one narrow-beam ultrasound transducer fixed on a support block provided with rotation means to rotate said at least one narrow-beam transducer in a direction of said duct and to position said at least one narrow-beam transducer with its narrow beam cutting said duct according to a cutting plane substantially perpendicular to the longitudinal axis of said duct;

(b) at least one wide-beam ultrasound transducer mounted in said probe to have its wide beam in a known relative position with respect to that of said at least one narrow-beam ultrasound transducer, rotation means being also provided to rotate said at least one wide-beam ultrasound transducer in the direction of said duct to measure, by the Doppler effect, the speed of said fluid flowing in said duct;

(c) a control and processing unit comprising processing means for processing the characteristics of the signal(s) from said at least one narrow-beam transducer, and (d) said processing means further comprising means for calculating the distance range ($P_2-P_1$) corresponding to the proximal wall and the distal wall of said duct in the wide-beam plane performed by said at least one wide-beam transducer, from the knowledge of the known relative position between said at least one wide-beam ultrasound transducer and said at least one narrow-beam ultrasound transducer as well as the distance between the proximal position and the distal position of the wall of said duct calculated in the cutting plane of said at least one narrow-beam transducer, and selecting means for selecting the signals received by said at least one wide-beam transducer, in the distance range ($P_2-P_1$) determined by said processing means, thereby determining a substantially accurate measure of the speed of substantially all the fluid flowing in said duct.

28. A probe, according to claim 27, wherein said duct is a blood vessel and said probe is adapted to measure the flow of blood in said blood vessel.

29. A method of measuring the speed or the flow rate of a fluid comprising particles in suspension, flowing within a duct having a longitudinal axis and scanned by at least one ultrasound sensor, wherein said method comprises:

(1) providing a probe having a longitudinal axis and comprising:

(a) at least one narrow-beam ultrasound transducer fixed on a support block provided with rotation means to rotate said at least one narrow-beam transducer in a direction of said duct and to position said at least one narrow-beam transducer with its narrow-beam cutting said duct according to a cutting plane substantially perpendicular to the longitudinal axis of said duct, thereby defining a duct distal wall and a duct proximal wall;

(b) at least one wide-beam ultrasound transducer mounted in said probe to have its wide beam in a known relation position with respect to that of said at least one narrow-beam ultrasound transducer, rotation means being also provided to rotate said at least one wide-beam ultrasound transducer in the direction of said duct to measure, by the Doppler effect, the speed of said fluid flowing in said duct;

(c) a control and processing unit comprising processing means for processing the characteristics of the signal(s) from said at least one narrow-beam transducer;

(2) activating said rotation means to rotate said at least one narrow-beam ultrasound transducer while said at least one narrow-beam ultrasound transducer is emitting an ultrasound narrow beam until said at least one narrow-beam ultrasound transducer is in a position in which said narrow beam is cutting said duct according to a direction substantially perpendicular to said walls of said duct;

(3) activating said at least one wide-beam ultrasound transducer to emit a wide beam in said known relative position with respect to the position of said at least one narrow-beam ultrasound transducer resulting from step (2) hereabove, to measure, by the Doppler effect, the speed of said fluid flowing in said duct; and (4) processing with said processing means the characteristics of the signals from said at least one narrow-beam transducer and from said at least one wide-beam transducer to determine a substantially accurate measure of the speed of substantially all the fluid flowing in said duct.

30. A method of measuring the speed or the flow rate of a fluid comprising particles in suspension, flowing within a duct having a longitudinal axis and scanned by at least one ultrasound sensor, wherein said method comprises:

(1) providing a probe having a longitudinal axis and comprising:

(a) at least one narrow-beam ultrasound transducer fixed on a support block provided with rotation means to rotate said at least one narrow-beam transducer in a direction of said duct and to position said at least one narrow-beam transducer with its narrow-beam cutting said duct according to a cutting plane substantially perpendicular to the longitudinal axis of said duct, thereby defining a duct distal wall and a duct proximal wall;

(b) at least one wide-beam ultrasound transducer fixed on the support block to have its wide beam offset by a divergent angle relative to the narrow beam of said at least one narrow-beam ultrasound transducer, to measure, by the Doppler effect, the speed of said fluid flowing in said duct;

(c) a control and processing unit comprising processing means for processing the characteristics of the signals from said at least one narrow-beam transducer;

(2) activating said rotation means to rotate said at least one narrow-beam ultrasound transducer while said at least one narrow-beam ultrasound transducer is emitting an ultrasound narrow beam until said narrow beam is cutting said duct according to a direction substantially perpendicular to said walls of said duct;

(3) activating said at least one wide-beam ultrasound transducer to emit a wide beam in said known relative position with respect to the position of said at least one narrow-beam ultrasound transducer resulting from step (2) hereabove, to measure, by the Doppler effect, the speed of said fluid flowing in said duct; and (4) processing with said processing means the characteristics of the signals from said at least one narrow-beam transducer and from said at least one wide-beam transducer for determining the position of said at least one narrow-beam transducer for which echoes of the distal position are received at the amplitude maxima, and controlling with said control unit the working of said at least one wide-beam ultrasound transducer to measure the speed of said fluid flowing in said duct in that position of said at least one narrow-beam ultrasound transducer, thereby determining a substantially accurate measure of the speed of substantially all the fluid flowing in said duct.

31. A method of ascertaining the rate of liquid flow volume in a tubular member having a wall and a longitudinal axis, comprising the steps of:
(a) positioning a narrow beam transducer externally of said tubular member for producing an ultrasound beam having a width substantially less than the diameter of said tubular member;
(b) activating said narrow beam transducer to emit a narrow ultrasound beam into said tubular member;
(c) rotating said narrow beam transducer, about an axis substantially parallel to the longitudinal axis of said tubular member, to a position in which the magnitude of reflected ultrasound energy indicates perpendicularity of said narrow ultrasound beam to said wall of said tubular member; and
(d) measuring flow volume through said tubular member by activation of a wide beam transducer projecting a wide ultrasound beam passing through the entire width of the tubular member, said flow volume varying according to reflected ultrasound energy from said wide ultrasound beam.

32. A method, according to claim 31, wherein said tubular member is a blood vessel and said wide-beam transducer is adapted to measure the flow of blood in said blood vessel.

33. A probe, for accurately measuring the speed or the flow rate of blood flowing in a blood vessel having a longitudinal vessel axis, comprising:
(a) at least one rotatable narrow-beam ultrasound transducer having a beam cutting said blood vessel in a plane substantially perpendicular to said vessel axis and rotating about an axis substantially parallel to said vessel axis;
(b) at least one wide-beam ultrasound transducer for measuring the speed of blood flow in the vessel by the Doppler effect, said at least one wide-beam transducer being mounted in said probe in a known relative rotational position with respect to said at least one narrow-beam ultrasound transducer;
(c) a control and processing unit comprising processing means for processing signal(s) from said at least one narrow-beam transducer in order to receive speed measurement signals from said at least one wide-beam transducer when said at least one wide-beam transducer passes through the entire width of the blood vessel,
thereby determining a substantially accurate measure of the blood flowing in the blood vessel.

* * * * *